(12) United States Patent
Aslam et al.

(10) Patent No.: US 6,420,606 B1
(45) Date of Patent: Jul. 16, 2002

(54) METHOD FOR PRODUCING ALKOXY ARYLAMINE COMPOUNDS

(75) Inventors: Mohammad Aslam, Bridgewater; Patrick MacManus; Margaret Cullen, both of Morristown, all of NJ (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 09/602,772

(22) Filed: Jun. 23, 2000

Related U.S. Application Data

(60) Provisional application No. 60/141,188, filed on Jun. 25, 1999.

(51) Int. Cl.[7] ............................................. C07C 211/00
(52) U.S. Cl. ...................... 564/305; 564/336; 564/342; 564/343
(58) Field of Search ................................ 564/305, 336, 564/342, 343

(56) References Cited

U.S. PATENT DOCUMENTS

| | | | |
|---|---|---|---|
| 3,069,432 A | | 12/1962 | Yale |
| 4,124,640 A | * | 11/1978 | Shinohara et al. |
| 4,231,963 A | * | 11/1980 | Shinohara et al. |
| 4,268,458 A | * | 5/1981 | Shulte-Huermann et al. |

OTHER PUBLICATIONS

Ryuzaburo Nodzu et al, Studies on Chemotherapy of Tuberculosis IV. Synthesis of m–and p–aminophenol alkyl ethers and their bacteriostatic action on M. turbercolisis. J. Pharm. Soc. Japan 74(8) : 1984; p 872–875.*

P. Jacobson et al. "Notiz zur Kenntniss de Diaminophenole" Berichte der Deutschen Chemischen Gesellschaft, vol. 36, 1903, pp. 4124–4126.

H.L. Yale et al. "Novel polycyclic heterocycles. Derivatives of 5,11–dihydrodibenz[b,e][1,4]oxazepine and 5,11–dihydrodibenz[b,e][1,4]thiazepine," Journal of Medicinal Chemistry, vol. 13, No. 4, 1970, pp. 713–722.

A. Ek et al. "The synthesis of labile hydroxytryptophan metabolites," Journal of the American Chemical Society, vol. 76, No. 22, 1954, pp. 5579–5588.

J. Chem. Soc. Perkin Trans. I, 1127, 1990 (Conner, J.W.,; Leeming, S.W.)) Influence of Substrate Structure on on Copper (1)–assisted Cyanide Substitution in Aryl Halides.

* cited by examiner

*Primary Examiner*—Sreeni Padmanabhan
*Assistant Examiner*—Sikarl A. Witherspoon
(74) *Attorney, Agent, or Firm*—Colleen D. Szuch

(57) ABSTRACT

Disclosed are methods of producing of alkoxy arylamine compounds which find particular use in the syntheses of pharmaceutical drug. The alkoxy arylamine compounds generally have the formula:

$$H_2N-Ar-OR$$

wherein Ar is an unsubstituted or substituted aromatic group, and R is an unsubstituted or substituted alkyl or aryl group. The methods comprise generally, the steps of (a) alkylating a protected-amino arylalcohol to form a protected-amino arylether; and (b) deprotecting said protected-amino arylether to form an alkoxy arylamine compound.

10 Claims, No Drawings

METHOD FOR PRODUCING ALKOXY ARYLAMINE COMPOUNDS

This application claims priority from Provisional application Ser. No. 60/141,188, filed Jun. 25, 1999.

FIELD OF INVENTION

The present invention relates to methods for the production of alkoxy arylamine compounds.

BACKGROUND

Alkoxy arylamine compounds are of particular interest for use in the syntheses of numerous pharmaceutical drug candidates. For example, psychoactive drugs and other drugs used in the treatment of depression may be synthesized using alkoxy arylamine compounds.

Applicants believe that known methods for making alkoxy arylamine compounds exhibit certain drawbacks and inefficiencies. For example, U.S. Pat. No. 3,069,432, issued to Yale et al., discloses the synthesis of 2-(o-Bromobenzyloxy) aniline from o-nitrophenol and o-bromobenzyl bromide starting materials. The starting materials are first reacted in the presence of base to form a reaction product stream containing numerous components including an alkoxy nitroaryl compound. The Yale patent requires that the reaction product mixture be processed through filtering, washing and recrystallization in order to isolate the alkoxy nitroaryl compound for use in a subsequent reduction step in which the isolated alkoxy nitroaryl compound is reduced to an alkoxy arylamine compound using a large excess of iron powder in the presence of concentrated hydrochloric acid ("HCl").

The present inventors have come to appreciate that prior art processes of the type used by Yale et al. are disadvantageous for several reasons. For example, one disadvantage is that the Yale process requires isolation of the alkoxy nitroaryl compound in order to conduct the acidic reduction of the subsequent step. Such isolation techniques tend to be time-consuming and costly, and they tend to have a negative impact on the overall efficiency of the synthesis procedure. Another disadvantage of the prior art processes is that the use of stoichiometric amounts of metal, such as iron, creates a relatively large amount of waste which is potentially harmful to the environment. Accordingly, such use tends to require a relatively large amount of time and expense to purify the desired product and to dispose properly of the waste.

Recognizing these and other drawbacks of the prior art, the present inventors have perceived a need for a new, efficient and more desirable method for producing a wide range of alkoxy arylamine compounds.

DESCRIPTION OF THE INVENTION AND PREFERRED EMBODIMENTS

The present invention is directed to methods of producing a wide range of alkoxy arylamine compounds, many of which find particular use in the syntheses of pharmaceutical drug candidates such as psychoactive drugs. As used herein, the term "alkoxy arylamine compound" refers generally to amines having the formula:

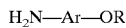

H$_2$N—Ar—OR wherein Ar is an unsubstituted or substituted aromatic group, and R is an unsubstituted or substituted alkyl, aralkyl or aryl group. The term "alkoxy arylamine compound" is also intended to encompass salts derived from amines of the formula noted above.

The present methods comprise generally, the steps of (a) alkylating a protected-amino arylalcohol to form a protected-amino arylether; and (b) deprotecting said protected-amino arylether to form an alkoxy arylamine compound. As used herein, the term "protected-amino arylalcohol" ("PAA") refers generally to a compound of Formula I:

Z—N(H)—Ar—OH                                    (I)

wherein Ar is an unsubstituted or substituted aromatic group which does not interfere with o-alkylation of the hydroxyl group and Z is an amine protecting group. Furthermore, as used herein, the term "protected-amino arylether" ("PAE") refers generally to a compound of Formula II:

Z—N(H)—Ar—OR                                    (II)

wherein R is an unsubstituted or substituted alkyl, aralkyl or aryl group.

In general, it is contemplated that the alkylation reaction of the present invention can be advantageously coupled with the deprotection reaction in a large number of circumstances and applications, and all such variations are within the scope of the present invention. In highly preferred embodiments, however, both the alkylation reaction and the deprotection reaction are solvent reactions. As used herein, the term "solvent reaction" refers to a reaction in which at least a portion of the reactants are solutes in a liquid phase solution. Furthermore, it is highly preferred that the deprotection reaction solution is compatible with the reaction solution used for the alkylation step. As used herein, the term "compatible solutions" refers to two or more reaction solutions which can be integrated, such as by mixing, without substantial degradation of the respective reactions occuring in each solution.

It will be appreciated that the use of compatible reaction solutions in accordance with the present invention has important advantages and desirable characteristics. In particular, the use of compatible reaction solutions contributes to the ability of the processes of the present invention to produce excellent yields and short overall reaction times without the need to isolate reaction products from solution between successive steps. As a result, it is possible that the alkylation step and the deprotection step can occur in the same reaction vessel. This not only provides a potentially important cost savings, it represents a potential improvement in the rate at which the desired compounds can be produced. In a batch-wise operation, the alkylation reaction can be allowed to continue to a high degree of completion, potentially even a substantial completion, at which point the reaction vessel is charged with the reactants and/or the reaction conditions in the vessel are changed so as to initiate the deprotection reaction. In view of the teaching herein, those skilled in the art can also readily appreciate that some degree of reaction overlap is thus possible to the extent consistent with other criteria for the production of the particular alkoxy arylamine compound that is desired.

The present methods can also be carried out with the same degree of flexibility in a continuous operating mode. For example, for embodiments in which the reaction vessel is a continuous tubular reactor ("CSTR"), the reactants necessary to initiate the alkylation reaction can be introduced into the vessel under conditions effective to initiate the alkylation reaction, which is allowed to continue for a sufficient residence time to achieve a high degree of reaction completion. The length along the tubular reactor at which the desired level of completion occurs can be readily determined, by calculation or by sampling, and the deprotection reactants can be introduced to the reactor at this location and/or the conditions in the reactor (such as reaction temperature) at this location can be altered (such as by heating or cooling) so as to initiate the deprotection reactions. It will be appreciated that the feed locations to a continuous stirred tank reactor, or any other type of continuous reactor, can be adjusted to initiate the deprotection reaction at the desired degree of completion of the alkylation reaction, as required for any particular application.

According to preferred embodiments, the alkylation reaction of step (a) comprises a solution reaction promoted by basic conditions and the deprotection reaction comprises a solution reaction promoted by basic conditions, that is, the alkylating and the deprotecting step each comprise reaction of the respective materials in the presence of basic reagents. Preferably, the alkylation solution and the deprotection solution are compatible solutions. As with the broad aspects of the present invention, the alkylation step and the deprotection step in such preferred embodiments can each be carried out in a batch mode, a continuous mode or a combination of batch and continuous modes.

Numerous other advantages are associated with the methods of the present invention. For example, by avoiding the use of metal-based compounds as essential elements in the reaction mechanism, the present invention is capable of avoiding the excessive clean-up and higher processing costs associated therewith. Furthermore, because alkoxy arylamine compounds can be synthesized according to the present invention without isolation of an alkoxy nitroaryl intermediate, a significant savings in plant processing time is achieved. Additionally, the present invention avoids the formation of excess impurities associated synthesis procedures which require both acid and base reagents. The present invention also has features which can potentially produce significant savings in the capital costs required to produce commercial quantities of alkoxy arylamine compounds.

Starting Materials
Formula I Compound

A wide variety of PAA's can be used as reactants in accordance with in the present invention. For example, in compounds corresponding to Formula I, Ar can be any unsubstituted or substituted aromatic group which does not interfere with o-alkylation of the hydroxyl group. Examples of aromatic groups adaptable for use in the present invention include: aryl groups such as phenyl, o-tolyl, m-tolyl, p-tolyl, o-xylyl, m-xylyl, p-xylyl, alpha-naphthyl, beta-naphthyl, o-anisyl, m-anisyl, p-anisyl and the like, and heteroaryl groups such as pyridinyl, pirimidinyl, quinolinyl, isoquinolinyl and the like. In preferred embodiments, the Ar group is an unsubstituted or substituted aryl group having from about six carbons to about 15 carbons such as phenyl, o-tolyl, m-tolyl, p-tolyl, o-xylyl, m-xylyl, p-xylyl, alpha-naphthyl or beta naphthyl, with unsubstituted or substituted aryl groups having from about six carbons to about eight carbons such as phenyl, o-tolyl, m-tolyl, p-tolyl, o-xylyl, m-xylyl, and p-xylyl being especially preferred.

The Z group in Formula I can be any suitable amine protecting group capable of being removed under basic or acidic conditions. As used herein, the term "amine protecting group" refers generally to any nitrogen-protecting group that is readily removable to form a free amine after generation of a protected-amino ether. Examples of suitable amine protecting groups which are removable under basic conditions include unsubstitued or substitued acyl groups such as acetyl, propanoyl, butanoyl, pentanoyl and the like, and aroyl groups such as benzoyl, o-chlorobenzoyl, m-chlorobenzoyl, p-chlorobenzoyl, o-nitrobenzoyl, m-nitrobenzoyl, p-nitrobenzoyl and the like. Examples of suitable amine protecting groups removable under acidic conditions include carbamates such as tert-butoxycarbonyl, with acyl or aroyl groups of about two to about seven carbons such as acetyl and benzoyl being especially preferred.

In preferred embodiments, the protected amine group and the hydroxyl group of the PAA are situated ortho with respect to each other. However, it is contemplated that in other embodiments, the PAA of the present invention may comprise a protected amine group and a hydroxyl group which are not in ortho positions.

Alkylating Agent

As mentioned above, the present invention involves reacting a compound of Formula I with an "alkylating agent". As used herein, the term "alkylating agent" refers to any material capable of providing to the reaction a electrophilic alkyl, aryl, aralkyl or cycloalkyl R group capable of reacting with the hydroxyl group of the compound of Formula I to form a compound of Formula II. The electrophilic R group provided by the alkylating agent or agents may be unsubstituted or substituted and may contain heteroatoms. Examples of suitable alkylating agents include: aryl halides such as 2-Bromobenzyl bromide, 2-Bromobenzyl chloride and the like; and alkyl halides such as propyl iodide, cyclohexyl bromide, octyl bromide, cyclopentylmethyl bromide, with aryl halides such as 2-Bromobenzyl bromide being especially preferred.

Basic Reagents

A wide variety of bases known in the art are available commercially and can be used as reagents in the processes of the present invention. Examples of bases for use in the present invention include: hydroxide salts, such as potassium hydroxide and sodium hydroxide; carbonate salts, such as potassium carbonate and sodium carbonate; metal alkoxides, such as sodium ethoxide, sodium methoxide, potassium tert-butoxide, soidum terpineolate; and the like. Furthermore, mixtures of these bases may also be used in the present invention. According to certain embodiments, hydroxide salts are prefered.

In general, it is desirable to use a base which has a pKa about equal to or greater than the pKa of the hydroxyl proton of the Formula I compound. In general, such a requirement ensures that the base will be effective in deprotonating the alcohol to affect the formation of an alkoxy salt. Accordingly, the base chosen depends in part on the starting materials used. For example, in preferred embodiments wherein the compound of Formula I is 2-Acetamidophenol, wherein the hydroxyl proton has a pKa of about 10, a base having a pKa of at least about 9 or higher is preferably used.

Moreover, it has been found that for many embodiments, as the basic strength increases, the overall yield of alkoxy arylamine compound increases. Although the present inventors do not wish to be bound by or to any theory of operation, it is believed that the stronger bases more readily form the salts of compounds of Formula I, which results in greater yields of the corresponding products. Accordingly, in particularly preferred embodiments of the present invention, the base is a relatively strong base such as potassium hydroxide or sodium hydroxide.

In view of the teachings contained herein, one of ordinary skill in the art will be readily able to select a base for use in accordance with any particular application of the present invention.

Alkylation Reaction Conditions

The alkylation reaction of the present invention is conducted under conditions effective to convert at least a portion of the Formula I starting material, and preferably at least a major proportion of the Formula I compound to an alkoxy compound of Formula II. In preferred embodiments, the process of the present invention is conducted without isolation of the product of Formula II. For such embodiments, it is preferred that at conversion of at least about 90% (on a mole basis) of Formula I compound is achieved.

For the relatively unpreferred embodiments in which the compound of Formula II is to be isolated prior to the deprotection step, the conversion of the compound of Formula I can be less than about 90% (on a mole basis), with conversion as low as about 80% being acceptable.

In general, it is contemplated that the particular temperatures, pressures and other reaction conditions can vary widely within the scope of the present invention, depending on factors such as the particular starting material being used, the process equipment available and the particular alkoxy compound that is desired. In general, the alkylation reaction is preferably carried out at temperatures of from about 55° C. to about 225° C., even more preferably from about 65° C. to about 175° C., and at pressures of from about 0.5 atmospheres ("atm") to about 2.0 atm, even more preferably about 0.75 atm to about 1.25 atm.

With respect to the relative amounts of starting materials to be used in the alkylating step of the present invention, it is believed that this can also vary widely depending on the particulars of each application, including the particular compound of Formula I. For example, for preferred processes in which the Formula I compound comprises 2-Acetamidophenol and the alkylating agent is 2-Bromobenzyl bromide, the mole ratio of Formula I compound to alkylating agent is preferably at least about 1:2, more preferably at least about 1:1.5, and even more preferably at least about 1:1.

The relative amount of base to be used in the alkylating step of the preferred practice of the present invention can also vary widely within the scope hereof. However, for preferred processes in which the Formula I compound comprises 2-Acetamidophenol and the alkylating agent is 2-Bromobenzyl bromide, the mole ration of Formula I compound to base is preferably at least about 1:2, more preferably at least about 1:1.5, and more preferably at least about 1:1.

According to certain preferred embodiments of the present invention, the alkylating step (a) comprises a basic solution reaction, that is a reaction in which a compound of Formula I reacts with an alkylating agent and a base in the presence of a solvent. Any suitable solvent in which each of the PAA, alkylating agent and base reagents are relatively soluble are preferred for this purpose. Examples of solvents adaptable for use in the present invention include: alcohols such as ethanol, isopropanol, isoamyl alcohol, n-butanol, tert-butanol and the like; and aprotic solvents such as N,N-dimethylformamide, N-methylpyrrolidine, dimethyl sulfoxide, 1,3-dimethyl-3,4,5,6-tetrahydro-2(1H)-pyrimidinone ("DMPU"), with alcohols such as ethanol, isopropanol, isoamyl alcohol, n-butanol, tert-butanol and the like being especially preferred.

Temperature and Time

The temperature and time of the alkylation reaction can vary within the scope hereof, depending on numerous factors, including the particular starting materials used and whether the process is carried out in a batch mode, in a continuous mode or in a combination of batch and continuous modes. For batch processes in which the Formula I starting material is 2-Acetamidophenol and the alkylating agent is 2-Bromobenzyl bromide, it is preferred that the alkylation reaction be carried out under reflux conditions, preferably until at least a portion of the starting materials are consumed. More preferably, the reaction is heated to reflux until substantially all of the starting materials are consumed.

In certain preferred embodiments, the reaction product mixture produced in step (a) of the present invention is used as starting material in deprotection step (b) without substantial modification, and particularly preferably without isolation of the compound of Formula II. Once a desired amount of Formula II compound has been formed in step (a), the entire reaction product mixture, including substantially any impurities, may used as starting material to be subjected to step (b) deprotection conditions.

In other, less preferred, embodiments of the present invention, it is contemplated that the Formula II compound formed in step (a) may be purified, isolated and/or otherwise modified prior to use as starting materials in step (b). The Formula II compound produced via the present invention may be purified by conventional methods known to those skilled in the art. For example, aqueous washes, drying, concentrating under reduced pressure, crystallization, slurrying, chromatography and the like may be used.

The Deprotecting Step

The deprotecting step (b) of the present method preferably comprises subjecting a PAE to conditions effective to form therefrom an alkoxy arylamine compound. Such a deprotection reaction can occur in either basic or acidic conditions. As those of ordinary skill in the art will appreciate, the selection of basic or acidic conditions for use in the deprotecting step (b) should be selected to reflect conditions under which the amine protecting group (Z) is removed relatively readily to form an alkoxy arylamine compound.

Basic Deprotection Conditions

In certain preferred embodiments, the deprotecting step comprises reacting a PAE with a base in a solvent to form an alkoxy arylamine compound. Any of the aforementioned bases for use in step (a) of the present invention can be used for step (b). The base used will depend on a number of factors, including the particular Formula II compound involved. In general, it is preferred that the reaction conditions are sufficiently basic to remove the acyl group and replace it with a hydrogen group. For example, in preferred embodiments wherein the Formula II compound comprises an ether formed from 2-Acetamidophenol and 2-Bromobenzyl bromide, the deprotecting base is preferably one having a pKa of at least about 9, such as potassium hydroxide, sodium hydroxide, potassium carbonate or sodium carbonate. A particularly preferred base is potassium hydroxide.

Furthermore, according to preferred embodiments of the present invention, the base used in step (b) comprises substantially the same base used in step (a).

The relative amount of base to be used in the preferred practice of the present invention can vary widely within the scope hereof, depending on a number of factors including the Formula II compound involved. However, for preferred processes in which the Formula II compound comprises an ether formed from 2-Acetamidophenol and 2-Bromobenzyl bromide, the mole ratio of Formula II compound to base is preferably at least about 1:9, more preferably at least about 1:7, and more preferably at least about 1:5.

Any of the aforementioned solvents for use in step (a) of the present invention can be used for step (b). In a preferred embodiment, the solvent used in step (b) is substantially the same solvent used in step (a).

The temperature and time of the deprotection reaction can vary within the scope hereof, depending on numerous factors, including the particular starting materials used. For batch processes in which the Formula II material is an ether formed from 2-Acetamidophenol and 2-Bromobenzyl bromide, it is preferred that the reaction be heated to reflux until at least a portion of the Formula II compound is consumed. More preferably, the reaction is heated to reflux until substantially all of the Formula II compound is consumed.

According to embodiments of the present invention wherein the deprotection step (b) comprises conducting a solution reaction under basic conditions, the alkoxy arylamine compound produced may be purified by conventional methods known to those skilled in the art. For example, aqueous washes, drying, concentrating under reduced pressure and the like may be used.

Moreover, in certain preferred embodiments, the method of the present invention involves the deprotection step (b) producing a "free amine" alkoxy arylamine and further comprises the step (c) of converting the "free amine" alkoxy arylamine product to an alkoxy arylamine-HCl salt. Because such salts tend to be crystalline, they are more stable and can be purified via recrystillization. Additionally, free alkoxy arylamines tend to be unstable. Accordingly, it is often desirable to convert alkoxy arylamine products to their HCl salts. Any method for converting amines to their corresponding HCl salts known to those skilled in the art can be used in the present invention. For example, in preferred embodiments of the present invention wherein the alkoxy arylamine compound produced is 2-(o-Bromobenzyloxy) aniline, said compound can be separated from the reaction mixture into an organic solvent such as Methyl-tert-butyl ether, and subsequently washed with aqueous HCl solution to form the HCl salt. In light of the teachings herein, those of skill in the art will be readily able to optimize conditions for converting free amine alkoxy arylamines produced according to the present invention to their corresponding HCl salts.

Acidic Deprotection Conditions

In certain other embodiments of the present invention, the deprotecting step comprises reacting a protected-amino arylether under acidic conditions to form an alkoxy arylamine compound.

A wide variety of acids known in the art are available commercially and can be used as reagents in the processes of the present invention. Examples of acids for use in the present invention include trifluoroacetic acid and aqueous mineral acids such as, sulfuric acid and HCl. In certain embodiments, the use of HCl is especially preferred because, in addition to deprotecting the amine moiety, it further affects the formation alkoxy arylamine-HCl salts, which, as discussed above, are desirable target molecules. For example, in preferred embodiments wherein the Formula II compound comprises an ether formed from 2-Acetamidophenol and 2-Bromobenzyl bromide, the deprotecting acid is preferably hydrochloric acid. In light of the teachings herein, those of skill in the art will be readily able to select an acid for use in the present invention without undue experimentation.

The relative amount of acid to be used in the preferred practice of the present invention can vary widely within the scope hereof, depending on a number of factors including the Formula II compound involved. In general, it is preferred to use an amount of acid sufficient to remove the amine protecting group and to form an alkoxy arylamine salt. For example, for preferred processes in which the Formula II compound comprises an ether formed from 2-tert-butoxycarbonylaminophenol and 2-Bromobenzyl bromide having a tert-butoxycarbonyl amine protecting group, it is desirable to add sufficient acid to bring the pH of the reaction mixture to about 4 or lower. Those of skill in the art will be readily able to determine the amount of acid for use in the present invention without undue experimentation.

A wide range of methods for deprotecting amines under acidic conditions can be used in the present invention. In certain preferred embodiments, the acidic deprotection step comprises washing an organic solution comprising a PAE with an acid solution. For example, in preferred embodiments of the present invention wherein the PAE comprises an ether formed from 2-Acetamidophenol and 2-Bromobenzyl bromide, said compound can be dissolved into an organic solvent such as Methyl-tert-butyl ether, and subsequently washed with aqueous HCl solution to form the HCl salt. In light of the teachings herein, those of skill in the art will be readily able to optimize conditions for deprotecting PAE compounds under acidic conditions to form alkoxy arylamine compounds.

Preferred Embodiments

According to preferred embodiments, the alkylating step (a) of the present invention further comprises the step of introducing the Formula I compound, alkylating agent and base into a reaction vessel. Any known reaction vessel can be used in the practice of the present invention. For example, when the process of the present invention is performed as a batch process, the reaction vessel may comprise a flask, kettle, autoclave and the like. When the process of the present invention is conducted as a continuous process, the reaction vessel may comprise, for example, a tubular reactor, a CSTR and the like.

Additionally, in preferred embodiments of the present invention, the reacting step (b) further comprises introducing base to the reaction vessel of step (a) after a predetermined time.

EXAMPLE

In order to illustrate, in a non-limiting manner, the present invention is described in connection with the following example which illustrates the synthesis of 2-(o-Bromobenzyloxy) aniline HCl salt according to a preferred embodiment.

To a 500 mL, 3-neck round-bottomed flask equipped with a mechanical stiffer, a condenser and a thermometer was charged 23.6 grains (0.156 mol) of 2-Acetamidophenol in 300 mL of ethanol (200 proof). 41.02 grams (0.164 mol) of 2-Bromobenzyl bromide was added, followed by the addition of 21.24 grains (1.09 molar equivalents) of potassium hydroxide ("KOH") in a 45% aqueous solution which formed a clear reaction solution. The reaction solution was heated to reflux for several hours until the starting materials were consumed. Additional KOH (6.0 molar equivalents) was then added and the reaction mixture was further heated for several hours to form 2-(o-Bromobenzyloxy) aniline. The reaction mixture was cooled and about 3/4 of the ethanol was removed under vacuum at 30–40° C. Methyl-tert-butyl ether ("MTBE") (200 mL) and water (300 mL) was added, the resulting layers were mixed and the lower aqueous layer was separated from the product-rich MTBE layer. The water layer was washed with MTBE (100 mL) and the MTBE layers were combined. The combined MTBE layers were washed with water (150 mL). Then, to the MTBE layers was added slowly 17.4 grams of HCl (1.0 molar equivalent) in a 37% aqueous solution to crystallize the product. The resulting crystal slurry was cooled to 0° C. and stirred for 1 hour. The crystals were filtered and washed with 30 mL of ice-cold ethanol and twice with 30 mL portions of ice-cold MTBE. The crystals were dried under nitrogen and vacuum to yield 41.5 grams (84% yield by weight) of 2-(o-Bromobenzyloxy) aniline HCl salt in 99.02% purity.

Having thus described a few particular embodiments of the invention, various alterations, modifications and improvements will readily occur to those skilled in the art. Such alterations, modifications and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A method for producing a compound of the formula $H_2N$—Ar—OR, wherein Ar is an unsubstituted or substituted aromatic group and R is an unsubstituted or substituted alkyl, aralkyl or aryl group, comprising the steps of:
   (a) reacting a protected-amino arylalcohol with an alkylating agent in the presence of a base and a solvent to form a reaction mixture comprising a protected-amino arylether; and
   (b) deprotecting said protected-amino arylether by introducing to said reaction mixture comprising a protected-amino arylether one or more reactants prior to any substantial step comprising isolation of said protected amino arylether.

2. The method of claim 1 wherein said deprotection step begins substantially only after said reaction step (a) is substantially complete.

3. The method of claim 1 wherein said deprotection step comprises introducing to said reaction mixture comprising a protected-amino arylether a base which is substantially the same or different from the base used in said reaction step (a).

4. The method of claim 3 wherein the base introduced to said reaction mixture comprising a protected-amino arylether is substantially the same base used in said reacting step (a).

5. The method of claim 4 wherein said base used in said reacting step (a) is selected from the group consisting of hydroxide salts, carbonate salts, metal alkoxides and mixtures of two or more thereof.

6. The method of claim 5 wherein said base used in said reacting step (a) is a hydroxide salt.

7. The method of claim 2 wherein said alkylating agent or arylating agent is 2-Bromobenzyl bromide or 2-Bromobenzyl choride.

8. The method of claim 1 wherein said protected-amino arylalcohol comprises a compound of the formula Z—N(H)—Ar—OH; wherein Z is an amine protecting group, Ar is a substituted or unsubstituted aromatic group, and the protected amino and hydroxyl groups are in an ortho position on said aromatic group.

9. The method of claim 8 wherein said Ar group is phenyl.

10. The method of claim 9 wherein said Z group is an acyl group.

* * * * *